(12) United States Patent
Sullivan

(10) Patent No.: US 6,406,854 B1
(45) Date of Patent: Jun. 18, 2002

(54) METHOD AND COMPOSITIONS FOR EVALUATING RESOLUTION OF NUCLEIC ACID SEPARATION SYSTEMS

(75) Inventor: Daniel E. Sullivan, Cambridge, MA (US)

(73) Assignee: MJ Research, Waltham, MA (US)

( * ) Notice: Subject to any disclaimer, the term of this patent is extended or adjusted under 35 U.S.C. 154(b) by 0 days.

(21) Appl. No.: 09/661,600

(22) Filed: Sep. 14, 2000

Related U.S. Application Data

(60) Provisional application No. 60/154,522, filed on Sep. 16, 1999.
(51) Int. Cl.[7] .......................... C12Q 1/68; C07H 19/00
(52) U.S. Cl. .......................................... 435/6; 536/22.1
(58) Field of Search .................... 435/6, 91.2; 536/22.1

(56) References Cited

PUBLICATIONS

Huang CH and Blumenfeld OO. Multiple origins of the human gycophorin St gene– identification of hot spots for independent unequal homologous recombinations. J.Biol. Chem., 266(34): 23306–23314, 1991.*

Fu TJ and Seeman NC. DNA double–crossover molecules. Biochemistry, 32(13): 3211–3220, 1993.*

* cited by examiner

*Primary Examiner*—Eggerton A. Campbell
*Assistant Examiner*—Brabha Chunduru
(74) *Attorney, Agent, or Firm*—Lahive & Cockfield, LLP; Thomas V. Smurzynski; Sean D. Detweiler

(57) ABSTRACT

Disclosed are methods and compositions for estimating the crossover point of a molecular separation system.

20 Claims, 2 Drawing Sheets

METHOD AND COMPOSITIONS FOR EVALUATING RESOLUTION OF NUCLEIC ACID SEPARATION SYSTEMS

RELATED APPLICATIONS

This application claims priority to U.S. Ser. No. 60/154,522, filed Sep. 16, 1999. The contents of this application are incorporated by reference in their entirety.

FIELD OF THE INVENTION

The invention relates to methods and compositions for measuring the resolution of molecular separation systems, such as polyacrylamide gels.

BACKGROUND OF THE INVENTION

Systems for separating and resolving nucleic acids employ many different technologies and are used for many different purposes. Separation technologies include, e.g., chromatographic methods such as High Performance Liquid Chromatography (HPLC), mass spectrometry methods such as Matrix-Assisted Laser Desorption—Time-of-Flight (MALDI-TOF), both of which are principally used for resolving small (<1000 base) nucleic acids. Another separation technology is electrophoresis. Electrophoresis can be further divided into low-voltage techniques, for resolving large molecules, typically employing agarose as a separation matrix; and high-voltage applications, for resolving small molecules, typically employing polyacrylamide derivatives as a separation matrix.

All of the above techniques separate different molecular species based on differential migration rates. The results of all of these techniques can be represented by a plot of the amount of a molecular species as a function of either migration time to a fixed or mobile reference point, or of distance migrated in a fixed time. In either case the position of the peak concentration in time or distance, is characteristic for each different concentration reaches a peak at a characteristic time or distance, for each different nucleic acid molecular species. Typically, the peak approximates a gaussian curve, and the distance between peaks is measured from the highest point of each peak. The capability to distinguish molecules of different sizes is called "resolution." Resolution (R) is usually expressed by the mathematical formula $$R = d/w$$

where d is the distance from the signal peak representing a molecular species to the signal peak representing a molecular species differing in length by a single nucleotide, and w is the average fall width at half maximum (FWHM) for the peaks.

In typical separation systems, d decreases and h increases as the separated molecules increase in size. Plots of d and h against molecular size generate two curves that cross at the point where d=h, and therefore R=1, defining the "crossover point" of the particular separation system employed.

In a separation application that results in even peak heights, if R>1, the sum of the signal in between two adjacent peaks must at some point be less than the height of either peak; thus there will be at least a small dip in the trace between the two peaks. Similarly, when R<1, two adjacent peaks will merge into an apparent single peak.

Different applications have different resolution requirements. Some applications, such as DNA and RNA sequencing, high-accuracy genotyping, and some forms of mutation detection (Oeffner reference) require single-base resolution (i.e., R>1) in at least part of the separation range. Other applications, such as genotyping by determining the number of dinucleotide, trinucleotide or tetranucleotide repeats present at a locus, require minimum resolution of 2, 3, and 4 bases, respectively (R=0.5, 0.33, and 0.25) throughout their usefull ranges.

In typical separations, R reaches its maximum value at small molecular sizes, and drops dramatically at larger molecular sizes. Furthermore, values of R achieved in a separation can be adversely affected by problems with equipment, reagents, and protocols. A reliable measure of system performance is to measure the point at which R=1, which is often referred to as the "crossover point". This value is typically expressed as the number of nucleotides corresponding to the position at which the curve for peak spacing, d, crosses the curve for peak width, h.

In developing, evaluating, and testing nucleic acid sequencing systems, determination of the crossover point is desirable, because the crossover point is directly related to the sequencing read length a system can deliver. Measurement of the crossover point is not usually performed using the output of a sequencing system in normal operation because of the difficulty in measuring FWHM values.

Instead, system performance is assayed by running sequencing reaction products of a DNA molecule of known sequence on the system and the number of high-confidence correct base determinations is counted. This method produces results that are confounded by variations in DNA sequencing chemistry and reaction quality. In addition, the resulting quality measures can not easily be compared in different locations and different times, because they are particular to the computer software used to perform the base sequence determination.

SUMMARY OF THE INVENTION

The invention is based in part on the discovery of methods for measuring the crossover point of molecular separation systems, and of compositions useful for measuring the crossover point. The methods and compositions allow for rapid, routine, and reproducible estimations of the crossover point of a separation system. In addition, the invention provides a method of assessing the quality of electrophoretic separation that is independent of any particular chemistry, reaction conditions, or software analysis program.

In one aspect, the invention provides a method for estimating the crossover point of a polymer separation system by electrophoresing a plurality of polynucleotide pairs, which can be alternatively referred to as crossover standards, through a polymer separation system. Each polynucleotide pair includes a first polynucleotide and a second polynucleotide. A signal associated with the first polynucleotide and a signal associated with the second polynucleotide in each polynucleotide pair is then detected. Next, a first polynucleotide pair is identified in which the signal associated with the first polynucleotide of the pair is not resolved from, or is coincident with, the signal associated with the second polynucleotide of the polynucleotide pair. A second polynucleotide pair is also identified in which the signal associated with the first polynucleotide of the pair is resolved from the second polynucleotide of the pair. Next, a region in the polymer separation system corresponding to that part of the system containing components migrating between the first polynucleotide pair and the second polynucleotide pair is identified. This region corresponds to the location of the crossover point in the polymer separation system.

In a preferred embodiment, the invention includes a method for estimating the crossover point of a polyacrylamide or polyacrylamide derivative-based separation system by electrophoresing a plurality of polynucleotide pairs through a polyacrylamide separation system. Each polynucleotide pair consists of a first labeled polynucleotide consisting of a core sequence and a second labeled polynucleotide consisting of the core sequence and an extension sequence, e.g., a one nucleotide extension sequence.

Also provided by the invention are compositions and kits that include polynucleotide pairs useful for estimating a crossover point in a separation system.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
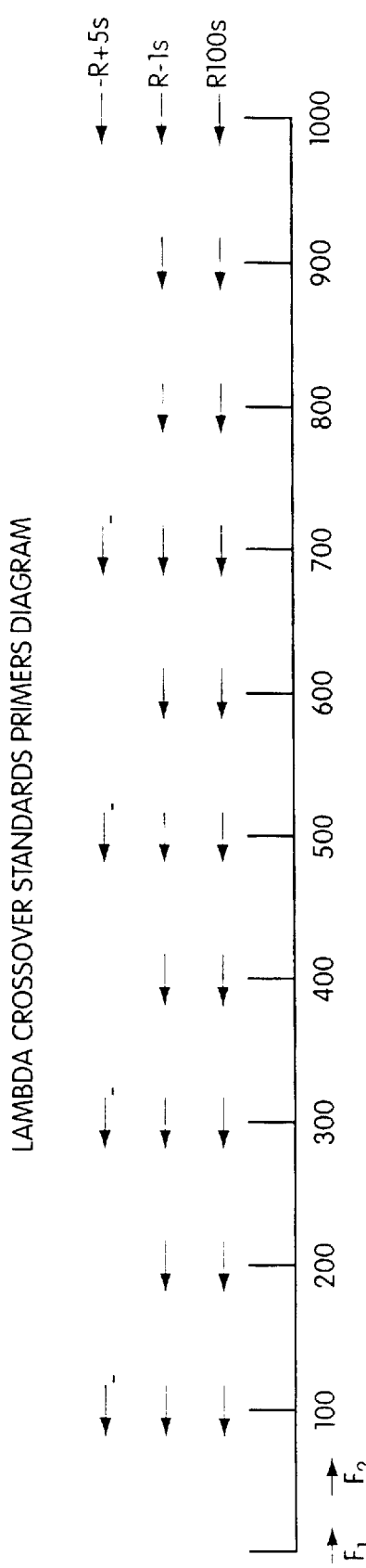
FIG. 1 is an illustration of polynucleotide pairs used for estimating the crossover point of a molecular separation system.

Crossover points are identified according to the invention by examining migration of members of two or more polynucleotide pairs through a nucleic acid separation system in which determination of the crossover point is desired. Members of a polynucleotide pair that migrate above the crossover point of the system will generate signals that are not resolved from each other. In contrast, members of a polynucleotide pair that migrate below the crossover point of the system will generate distinct signals. The crossover point of the system can be estimated by identifying the region of the separation system residing between polynucleotide pairs generating non-resolved signals and polynucleotide pairs generated resolved signals generate signals that are not resolved from each other. In contrast, members of a polynucleotide pair that migrate below the crossover point of the system will generate distinct signals. The crossover point of the system can be estimated by identifying the region of the separation system residing between polynucleotide pairs generating non-resoled signals and polynucleotide pairs generated resolved signals.

The polynucleotide pairs include a first polynucleotide and a second polynucleotide. The length difference between the first and second polynucleotides in each pair is chosen based on the desired resolution of the system. If single nucleotide resolution is desired, the first and second polynucleotide in each polynucleotide pair differ in length by a single nucleotide. If two nucleotide resolution is desired, the first and second nucleotide in each polynucleotide pair differ by two nucleotides. In general, if resolution for n nucleotides is desired, the first and second polynucleotide in each pair differ in length by n nucleotides. Crossover points based on two-nucleotide, three-nucleotide, or four nucleotide resolution may be desirable in applications in which genotyping by determining the number of dinucleotide, trinucleotide or tetranucleotide repeats, respectively, is desired.

The first and second polynucleotides in each pair are preferably closely related in composition and length. In preferred embodiments, the first polynucleotide in a polynucleotide pair can include a core sequence, while the second polynucleotide in the polynucleotide pair includes the core sequence and an extension sequence added to a terminus of the core sequence. The length of the extension sequence is chosen based on the desired resolution at the crossover point. For most applications the extension sequence is typically a nucleotide less than ten nucleotides or less in length. In various embodiments, the extension sequence is one, two, three, four, five, six or seven nucleotides in length, when the desired resolution at the crossover point is one, two, three, four, or five nucleotides, respectively.

When the first and second polynucleotides in a pair share a common core sequence, differences in migration rates caused by differences in sequence and labeling are eliminated. The only difference between the two sequences in a pair is in the extension nucleotide or nucleotides, which are preferably present at one end.

A polynucleotide pair is preferably combined with other polynucleotide pairs having members of different sizes. Preferably, multiple pairs of nucleic acids spaced at regular length intervals within the size region of interest are used. While any desired spacing is suitable, in various embodiments members of different polynucleotide pairs can differ in size by 25 nucleotides, 50 nucleotides, 100 nucleotides, etc. The size difference is determined using the size difference in size between the shorter polynucleotide in each pair, or between the longer polynucleotide in each polynucleotide pair. The set of pairs will in general be chosen to bracket the size at which the crossover point is suspected. In applications where the crossover point is believed to be between the migration position of nucleotide between 150 and 1300 nucleotides in length, a suitable set of polynucleotide pairs includes those having first and second nucleic acids having lengths of, e.g., 49 and 50 nucleotides, 99 and 100 nucleotides, 149 and 150 nucleotides, continuing at 50 nucleotide intervals about to 1499 and 1500 nucleotides.

In general, multiple polynucleotide pairs spanning a range of sizes are electrophoresed through a polymer separation system. In various embodiments, 2, 3, 5, 8, 10, 15, 20, 30, 45 or 50 or more pairs are electrophoresed through the molecular separation system.

The polynucleotide pairs are introduced into the molecular system at the origin and separated. Preferably, separation is by electrophoresed. The polymer separation system can be any separation system known in the art for high resolution separation of nucleic acids. The polymer system can include a DNA sequencing system. DNA sequencing systems include electrophoresis and detection hardware, any associated software, and reagents and methods used in system operation. Commonly used sequencing systems include an electrophoresis device employing a detector at a fixed distance from the place where the sample is introduced. In some embodiments, the separation system is a separation system based on polyacrylamide or derivatives of polyacrylamide. Other separation technologies include those suitable for high resolution separation technologies, such as HPLC, mass spectrometry, Matrix-Assisted Laser Desorption—

Time-of-Flight (MALDI-TOF) and high-voltage electrophoresis are all capable of single-base resolution, and are therefore suitable for employment with the invention.

Polynucleotide pairs are introduced into the polymer separation system, e.g., by addition to a dedicated separation channel of a separation system. The pairs are preferably introduced and separated in the manner normally used for samples being electrophoresed.

After electrophoreses, or contemporaneous with electrophoreses, the position of each nucleic acid in each pair in the separation system is determined. Polynucleotides can be detected using any method known in the art for identifying nucleic acids. Preferably, however, the polynucleotides are identified by identifying signals associated with each member of a polynucleotide pair. Suitable labels include, e.g., radiolabels and fluorescent labels. Fluorescent molecular tags suitable for labeling each of the four bases (see, e.g., Smith et al., U.S. Pat. No. 5,171,534). These tags are distinguished by color as they pass by the detector, thereby identifying the terminal nucleotide on the molecular species. The record of the colors detected as the molecules pass the detector can be detected with an electropherogram, in which the individual molecules are represented as a series of peaks.

For polynucleotide pairs migrating above the crossover point, i.e., between the origin and the crossover point, signals associated with each member of the polynucleotide pair will not be resolved. In contrast, signals will be resolved for polynucleotide pairs migrating below the resolution point, i.e., migrating such that the crossover point is between the origin and the polynucleotide pair. The crossover point can then be estimated as being within that region of the separation system containing components (e.g., nucleic acids) migrating between the polynucleotide pairs containing non-resolved signals and the polynucleotide pairs containing resolved signals.

The crossover point can be estimated with more certainty by examining the mobility of multiple polynucleotide pairs. The crossover point can be estimated as being within that region between the fastest migrating pair containing non-resolved signals and the slowest migrating pair containing resolved signals. For polynucleotide pairs very close to the crossover point, signals associated with first and second polynucleotides of polynucleotide pairs migrating very close to the crossover point will be nearly coincident.

If desired, the crossover point can be estimated using a single polynucleotide pair. Identification of non-resolved signals associated with each member of the polynucleotide pair indicates that the polynucleotide pair lies between the origin and the crossover point. Conversely, identification of resolved signals indicates that the crossover point is between the origin and the polynucleotide pairs.

At the completion of the separation procedure, the crossover point can be used to determine whether R was greater or less than the minimum desired value for any particular application.

In a preferred embodiment, the invention includes a method for estimating the crossover point of a polyacrylamide separation system by electrophoresing a plurality of polynucleotide pairs through a polyacrylamide separation system. Each polynucleotide pair consists of a first labeled polynucleotide consisting of a core sequence and a second labeled polynucleotide consisting of the core sequence and an extension sequence, e.g., a one nucleotide extension sequence.

The polynucleotide pairs can be used as crossover standards in a routine quality assurance program to ensure reproducibility of DNA sequencing systems. They can also be used to easily evaluate the effects of changes to the system, for example, different gel media or composition, a different sample preparation or run voltage regimen, etc.

Also within the invention is a kit that includes a plurality of polynucleotide pairs that can be used to estimate a crossover point in a molecular separation system. The polynucleotide pairs in the kit includes a first polynucleotide and a second polynucleotide. In preferred embodiments, the first polynucleotide consists of a core sequence and second polynucleotide consists of the core sequence and an extension sequence. In some embodiments, the first and second nucleotides in the pairs are labeled. In some embodiments, the extension sequence is one, two, three, four, or five nucleotides. Preferably, the kit includes at least 2, 5, 10, 15, 20, 25, 50, or more pairs of polynucleotides.

In various embodiments, the members of at least one polynucleotide pair differ by at least 10 nucleotides, 25 nucleotides, 50 nucleotides, or 100 nucleotides in size from the members of at least one second polynucleotide pair.

The invention will be further illustrated in the following non-limiting examples.

EXAMPLE 1

Generation of Crossover Standards for DNA Sequencing Systems

Polynucleotide pairs for estimating a crossover point were prepared using the polymerase chain reaction (PCR) process, using bacteriophage lambda DNA as a template. The bacteriophage lambda template was chosen because it is convenient and readily available; linear and thus a good template for PCR; and does not have an unusually high or low GC content. A set of PCR primers was specifically designed to generate labeled amplified molecules of the desired sizes. The primers used are set out in FIG. 1. Specifically, two forward primers (F1 and F2) were designed, with 5' nucleotides at positions 29404 and 29454, and with each primer 5' end-labeled with a fluorescent dye.

A set of forty labeled PCR products was generated by pairing each of these labeled primers with twenty unlabeled reverse primers. The reverse primers were designed so that they would amplify, when combined with F1, a series of molecules of lengths 99, 100, 199, 200, 299, 300 . . . up to a maximum value of 1000. The same set of primers, when combined with F2, would generate a series of molecules of length 49, 50, 149, 150 . . . up to 950. Thus, pairs of molecular species were prepared, beginning at lengths of 49 and 50 nucleotides and including pairs every 50 nucleotides up to 1000. In addition, molecules 5 nucleotides longer than the larger member of some pairs were included for rapid visual identification of sizes (105, 305, 505, 705, and 1005) in an electropherogram. These sets of molecules are called "Crossover Standards."

EXAMPLE 2

Use of Crossover Standards to Test a DNA Sequencing System

The crossover standards generated in Example 1 were run on a fluorescent DNA sequencing system. The resulting electropherogram displays well separated paired peaks until the crossover point is reached, at which point the two peaks have merged into a single peak.

Figure 2:
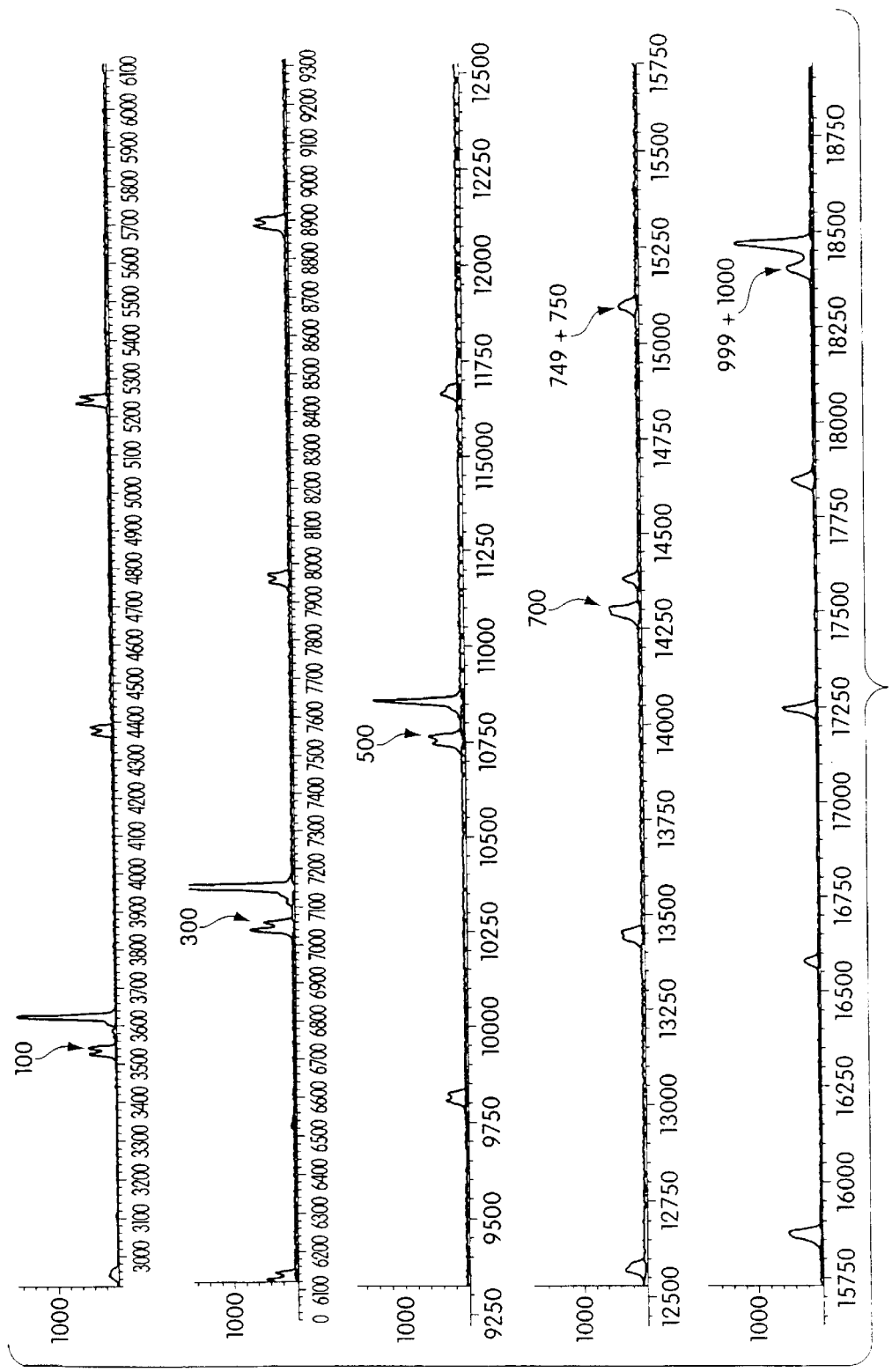
FIG. 2 is a representation of the results of running a set of polynucleotide pairs for estimating the crossover point of a molecular separation system.

The electropherogram of FIG. 2 shows the result of running the crossover standards obtained from Example 1 on a fluorescent DNA sequencing instrument. Shown is the amount of fluorescein label detected as a function of electrophoresis time. The data was obtained using a GeneSys Technologies, Inc. BaseStation instrument. The separation matrix was Long Ranger (FMC Corp.) used at 5%, the separation distance was 30 cm, and the electrophoresis voltage was 2900 V. Otherwise, standard conditions well known in the art were employed. The separation of the paired peaks is obvious from the smallest molecules shown, 99 and 100 bases, up to the peaks at 699 and 700 bases. The peaks at 749 and 750 bases and larger sizes are not resolved. Thus, a quick visual inspection of the data estimates a crossover point between 700 and 750 bases in this data set.

The descriptions given are intended to exemplify, but not limit, the scope of the invention. Other combinations of nucleic acid sizes and other means of manufacture, labeling, and separation are explicitly contemplated.

What is claimed is:

1. A method for estimating the location of the crossover point of a polymer separation system, the method comprising:

(a) electrophoresing a plurality of polynucleotide pairs through a polymer separation system, wherein each polynucleotide pair comprises a first polynucleotide and a second polynucleotide; and (b) detecting a signal associated with the first polynucleotide and a signal associated with the second polynucleotide in each polynucleotide pair;

(c) identifying a first polynucleotide pair in which the signal associated with the first polynucleotide of said first polynucleotide pair is not resolved from the signal associated with the second polynucleotide of said first polynucleotide pair;

(d) identifying a second polynucleotide pair in which the signal associated with the first polynucleotide of said second polynucleotide pair is resolved from the signal associated with the second polynucleotide of said second polynucleotide pair, and (e) identifying a region in the polymer separation system between the first polynucleotide pair and the second polynucleotide pair, thereby estimating the location of said crossover point in said polymer separation system.

2. The method of claim 1, wherein the polymer separation system is polyacrylamide.

3. The method of claim 1, wherein the first and second polynucleotide in each polynucleotide pair is labeled.

4. The method of claim 3, wherein the label is a radiolabel or a fluorescent label.

5. The method of claim 1, wherein the first and second polynucleotide differ in length by one nucleotide.

6. The method of claim 1, wherein the first polynucleotide in a polynucleotide pair consists of a core sequence and the second polynucleotide in said polynucleotide pair consists of said core sequence and an extension sequence.

7. The method of claim 1, wherein the extension sequence is 1 nucleotide.

8. The method of claim 1, wherein at least 3 polynucleotide pairs are electrophoresed through said polymer separation system.

9. The method of claim 1, wherein at least 5 polynucleotide pairs are electrophoresed through said polymer separation system.

10. The method of claim 1, wherein at least 10 polynucleotide pairs are electrophoresed through said polymer separation system.

11. The method of claim 1, wherein the members of at least one polynucleotide pair differ by at least 25 nucleotides in size from the members of at least one second polynucleotide pair.

12. The method of claim 1, wherein the members of at least one polynucleotide pair differ by at least 50 nucleotides in size from the members of a second polynucleotide pair.

13. The method of claim 1, wherein the members of at least one polynucleotide pair differ by at least 100 nucleotides in size from the members of a second polynucleotide pair.

14. A method for estimating the location of the crossover point of a polyacrylamide separation system, the method comprising:

(a) electrophoresing a plurality of polynucleotide pairs through a polyacrylamide separation system, wherein each polynucleotide pair comprises a first labeled polynucleotide consisting of a core sequence and a second labeled polynucleotide consisting of said core sequence and an extension sequence; and (b) detecting a signal associated with the first labeled polynucleotide and a signal associated with the second labeled polynucleotide in each polynucleotide pair; and (c) identifying a first polynucleotide pair in which the signal associated with the first polynucleotide of said first polynucleotide pair is not resolved from the signal associated with the second polynucleotide of said first polynucleotide pair; and (d) identifying a second polynucleotide pair in which the signal associated with the first polynucleotide of said second polynucleotide pair is resolved from the signal associated with the second polynucleotide of said second polynucleotide pair, and (e) identifying a region in the polymer separation system between the first polynucleotide pair and the second polynucleotide pair, thereby estimating the location of said crossover point in said polymer separation system.

15. The method of claim 1, wherein said extension sequence is one nucleotide.

16. A kit for estimating the location of the crossover point of a polymer separation system according to the method of claim 1, the kit comprising a plurality of polynucleotide pairs, wherein each polynucleotide pair comprises a first polynucleotide and a second polynucleotide, and wherein said first polynucleotide consists of a core sequence and second polynucleotide consists of said core sequence and an extension sequence.

17. The kit of claim 16, wherein said first and second nucleotides in said pairs are labeled.

18. The kit of claim 16, wherein the extension sequence is one nucleotide.

19. The kit of claim 15, wherein said kit comprises at least 5 polynucleotide pairs.

20. The kit of claim 16, wherein the members of at least one polynucleotide pair differ by at least 10 nucleotides in size from the members of at least one second polynucleotide pair.

* * * * *

UNITED STATES PATENT AND TRADEMARK OFFICE
CERTIFICATE OF CORRECTION

PATENT NO.    : 6,406,854 B1                                         Page 1 of 1
DATED         : June 18, 2002
INVENTOR(S)   : Daniel E. Sullivan It is certified that error appears in the above-identified patent and that said Letters Patent is hereby corrected as shown below:

Column 1,
Line 51, replace "the average fall width" with -- the average full width --

Column 3,
Lines 50-57, delete "generate signals that are not resolved from each other. In contrast, members of a polynucleotide pair that migrate below the crossover point of the system will generate distinct signals. The crossover point of the system can be estimated by identifying the region of the separation system residing between polynucleotide pairs generating non-resoled signals and polynucleotide pairs generated resolved signals."

Signed and Sealed this

Thirty-first Day of December, 2002

JAMES E. ROGAN
*Director of the United States Patent and Trademark Office*